(12) United States Patent
Colclough et al.

(10) Patent No.: US 10,588,748 B2
(45) Date of Patent: Mar. 17, 2020

(54) DEVICE TO FILL A BONE VOID WHILST MINIMISING PRESSURISATION

(71) Applicant: Biocomposites Limited, Keele, Staffordshire (GB)

(72) Inventors: John Warren Colclough, Keele (GB); Phillip Anthony Laycock, Keele (GB); John Joseph Cooper, Keele (GB); Russell David Waters, Keele (GB)

(73) Assignee: BIOCOMPOSITES LIMITED, Keele, Staffordshire (GB)

( * ) Notice: Subject to any disclaimer, the term of this patent is extended or adjusted under 35 U.S.C. 154(b) by 59 days.

(21) Appl. No.: 15/040,075

(22) Filed: Feb. 10, 2016

(65) Prior Publication Data

US 2016/0235534 A1   Aug. 18, 2016

(30) Foreign Application Priority Data

Feb. 17, 2015   (GB) .................................. 1502655.2

(51) Int. Cl.
| | |
|---|---|
| *A61F 2/28* | (2006.01) |
| *A61B 17/72* | (2006.01) |
| *A61B 17/70* | (2006.01) |
| *A61F 2/46* | (2006.01) |
| *A61B 17/68* | (2006.01) |
| *B29C 64/00* | (2017.01) |
| *A61B 17/92* | (2006.01) |
| *B29C 39/02* | (2006.01) |
| *B33Y 10/00* | (2015.01) |
| *B33Y 80/00* | (2015.01) |
| *B29L 31/00* | (2006.01) |

(52) U.S. Cl.
CPC ................ *A61F 2/28* (2013.01); *A61B 17/68* (2013.01); *A61B 17/7094* (2013.01); *A61B 17/72* (2013.01); *A61B 17/921* (2013.01); *A61F 2/4644* (2013.01); *B29C 39/026* (2013.01); *B29C 64/00* (2017.08); *A61F 2002/2835* (2013.01); *B29L 2031/7532* (2013.01); *B33Y 10/00* (2014.12); *B33Y 80/00* (2014.12)

(58) Field of Classification Search
USPC .... 623/13.11–13.14, 23.7–23.75; 606/92–93
See application file for complete search history.

(56) References Cited

U.S. PATENT DOCUMENTS

| | | | |
|---|---|---|---|
| 2003/0171811 A1* | 9/2003 | Steiner ...................... | A61F 2/08 623/13.17 |
| 2006/0200236 A1* | 9/2006 | Bianchi .................... | A61F 2/08 623/13.14 |
| 2008/0195204 A1* | 8/2008 | Zhukauskas .............. | A61F 2/08 623/13.14 |
| 2009/0192468 A1* | 7/2009 | Stone .................. | A61B 17/0401 604/174 |

OTHER PUBLICATIONS

Akhtar, "Fat Embolism" Anesthesiology Clin., vol. 27, 2009, pp. 533-550.

(Continued)

*Primary Examiner* — Yashita Sharma
(74) *Attorney, Agent, or Firm* — Tarolli, Sundheim, Covell & Tummino LLP (57) ABSTRACT

Disclosed is a device for implantation into a bone void while minimising the potential for an increase in pressure within the bone void.

16 Claims, 7 Drawing Sheets

(56) References Cited

OTHER PUBLICATIONS

Issack et al. "Fat Embolism and Respiratory Distress Associated with Cemented Femoral Arthroplasty" The American Jourlan of Orthopedics, vol. 38, No. 2, 2009, pp. 72-76.
Shaikh, "Emergency Management of Fat Embolism Snydrome" J. Emerg, Trauma Shock, 2009, pp. 29-33.
"Fat Embolism" J. Clin. Path., 23, Suppl. (Roy. Coll. Path), 4 pages, pp. 121-122.
Rebello, et al., "Venting Alone is Insufficient in Preventing Complications in the prophylactic Nailing of Femoral Metastases" Orthropaedic Biornechanics Laboratory, Sunnybrook & Women's College Health Sciences Centre, 49th Annual Meeting of the Orthopaedic Research Society, Poster #0997.
"Fat Embolism Syndrome" patientinfo/doctor/fat-embolismisyndrome.

\* cited by examiner

DEVICE TO FILL A BONE VOID WHILST MINIMISING PRESSURISATION

RELATED APPLICATIONS

The present application claims priority from United Kingdom Application No. 1502655.5, filed on Feb. 17, 2015, the subject matter of which is incorporated herein by reference

FIELD OF THE INVENTION

Bone substitute materials are increasingly being used for reconstruction or treatment of bone voids or bone defects. The bone substitute material may be in any one of a number of physical forms. During implantation it is essential for the surgeon to ensure that introduction of bone substitute material into a bone void does not pressurise the void site as pressurisation of the site may cause moderate to severe adverse effects for the patient.

The present invention provides an implantable device to be loaded into a void such as a long bone intramedullary canal (IM canal) while minimising the increase of pressure within the void, thus minimising the risk of embolization of the void contents into the bloodstream, which can have potentially fatal consequences for the patient.

BACKGROUND OF THE INVENTION

The use of bone substitute materials are common practice in orthopaedic surgical procedures for the filling of bony voids or to treat bone defects. These materials, following implantation, may resorb and be replaced by new bone as they do so. Bone substitute materials can be formulated as a paste that can be injected or digitally packed into open bone voids where they are allowed to cure in situ, or alternatively they can be moulded into solid implantable devices that can be packed into bone voids that are not intrinsic to the stability of the bony structure. It is important to ensure that the bone void does not become pressurised during insertion of the bone substitute material. This is particularly difficult to achieve if the bone void or defect is closed or contained.

Certain bone substitute materials are now increasingly being used to release therapeutic agents into bone void sites. These bone void sites may, for example, be infected sites and the therapeutic agents may be antimicrobials. Alternatively the medical condition may be a void created by a tumour and the therapeutic agent may be an antineoplastic or antiresorptive agent. Further, the therapeutic agent may stimulate new bone growth and be incorporated into the bone substitute material to enhance its osteogenic potential.

There are several methods in which surgeons will facilitate the placement of bone substitute material within a bone void or IM canal. For example, surgeons may inject a high viscosity bone substitute material into the bone void or IM canal until the void or IM canal is filled to its capacity with said bone substitute material.

Another method used by surgeons is to digitally pack a bone substitute material into the void again until said void is completely full.

This manner of placing the bone substitute material within a void and more specifically within the IM canal is known to increase the pressure within the void such that the increased pressure may result in an embolism, such as a fat embolism. Fat embolism syndrome (FES) is caused by fat droplets which are then found within the peripheral and lung microcirculation[1]. FES is a serious complication and can result in the death of the patient.

The pathologic significance of FES was first noted in 1862 by Zenker; however the first person considered to diagnose fat embolism was Von Bergmann in 1873, who reported on his findings concerning this condition[1,4].

As we are an aging population it means that the number of orthopaedic operations involving bone voids and more specifically the IM canal are increasing, thus increasing the risk of embolization or FES which in turn means an increase in perioperative cardiorespiratory emergencies[1].

Patients suffering from FES may be asymptomatic for a period of 12 to 48 hours before the clinical manifestations of the syndrome; these manifestations include but are not limited to tachycardia, petechial rash, elevated temperature (usually in excess of 38.3° C.), hypoxemia, and also neurological symptoms[6].

The mortality rate for patients suffering from FES is from 5-15%[3]; however proper treatment of the patient through ensuring good arterial oxygenation, the restriction of fluids and the use of diuretics which assist in minimising the accumulation of fluid in the patients lungs will assist in recovery.

There are several methods surgeons use to minimise pressure increases within a void or the IM canal which is being filled with bone substitute material; however, these methods to decrease pressure have been found to cause additional issues for both the surgeon and the patient.

One of these methods is to use a venting hole. This is where the surgeon drills a secondary opening within the long bone which is usually placed distal to the hole which the surgeon created for the placement of the bone substitute material. However, this method of reducing void or IM canal pressure has been found to have several issues. One of these issues is that the bone substitute material which the surgeon injects or digitally packs into the long bone may escape through the venting hole. This therefore means that an insufficient amount of bone substitute material may remain within the void or IM canal. Another issue found with this technique of using a venting hole to reduce void pressure is that it can cause injury to the patient's surrounding soft tissues[2] as well as increasing the risk of fracture at the site of the venting hole.

It has also been found that the use of this venting hole technique may not be sufficient on its own to maintain distal pressure below the point which would cause an embolism or the occurrence of FES[5] in the patient.

Therefore, the problem being addressed by the present invention is how to effectively and safely introduce bone substitute material, with or without a contained therapeutic agent therein, into a contained bony void in a patient, such as an IM canal, while ensuring that the bone void or defect does not become excessively pressurised, thus minimising the potential for embolization of the void contents into the patients' blood-stream.

SUMMARY OF THE INVENTION

Therefore, provided in accordance with the present invention is an implantable device for insertion into a bone void, the implantable device comprising a bone substitute material and having a longitudinal channel, where said longitudinal channel allows for depressurisation of the bone void during implantation of the device.

DISCLOSURE OF THE INVENTION

The present invention discloses an implantable device for insertion into voids or IM canal which provides a venting path for the displacement and exit of the contents of the void or IM canal. This helps to minimise any pressure increase within the void or IM canal and thus the potential for embolization of the void or IM canal contents.

The implantable device is typically, but not necessarily, spherocylindrical or capsule shaped, i.e. substantially cylindrical, having convex, domed or semispherical shaped ends. A longitudinally aligned channel, or a plurality of longitudinally aligned channels, extend the full length of any single device. The implantable device may have one or more of the longitudinally aligned channels. The device may be used alone or in combination with similar devices.

The longitudinal aligned channel(s) intersect the surface of the device and extend towards the device centreline. The depth of the longitudinal channel(s) may extend from the outer circumference to the axial centreline of the implantable device and is generally tapered such that the width of the longitudinal channel(s) opening on the outer, circumferential edge of the implantable device is greater than its width at its base, thus creating a continuous longitudinal channel or channels along the implantable device. The angular shaped longitudinal channel or channels of the implantable device preferably have an angle sized from about 10 degrees to about 145 degrees, more preferably about 20 degrees to about 50 degrees The continuous longitudinal channel(s) located longitudinally along the implantable device allows the exit of the void or IM canal contents as the implantable device(s) are inserted and/or advanced into the void or IM canal where they displace the contents of the void or the IM canal, thus allowing contents to escape the void or IM canal.

Figure 3A:
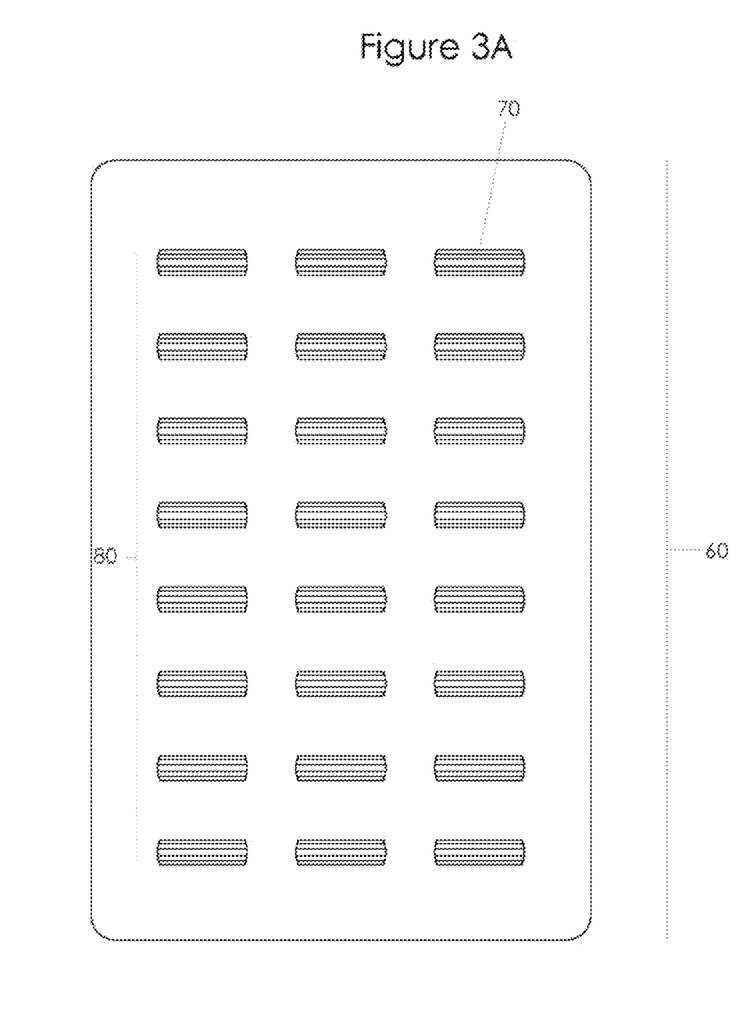
FIG. 3A shows a multi-cavity flexible mould mat with cavities that when filled with bone substitute material forms the implantable device.
Figure 3B:
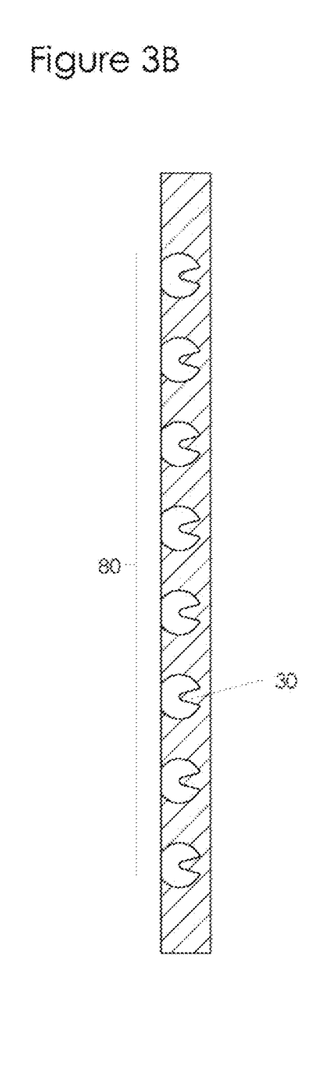
FIG. 3B shows a cross-section image of the multi-cavity flexible mould mat.

In one embodiment of the invention, for implantable devices that are produced using the mould of FIG. 3 herein, the opposing longitudinal side of the implantable device has a flat surface, which further allows for the displacement and escape of the void or IM canal contents.

The implantable device of the present invention is preferably about 5 mm to about 25 mm in diameter, more preferably about 7 mm to about 12 mm.

The overall length of the implantable device is preferably from about 6 mm to about 300 mm, more preferably about 10 mm to about 100 mm.

However, the diameter and length of the device is dependent upon the size of the bone void it is to be inserted into.

The longitudinal channel preferably has a taper angle of 10 degrees to 145 degrees, more preferably about 20 degrees to about 50 degrees.

The implantable device(s) of the present invention can be formed by several methods, including but not limited to, casting the implantable device in a multi-cavity flexible mould mat, or 3D printing the implantable device. Once formed by one of the methods disclosed above, the device(s) are ready to be implanted into a void or IM canal in a patient. This may be accomplished by digitally packing or by means of either a dispensing guide-wire or a guide tube. The implantable device(s) can be serially (i.e. all together) or sequentially (i.e. one at a time) inserted in their axial orientation into the bone void or IM canal.

A guide tube can be inserted into the void or IM canal and then loaded with implantable devices. Alternatively a guide tube can be first filled with one or more implantable devices, and the guide tube is subsequently inserted into the bone void or IM canal.

A non-rigid pusher can then be placed into the guide tube where it will make contact with the most proximal implantable device. The guide tube is then retracted whilst positive pressure is maintained on the pusher and the pusher maintains contact with the implantable device. This action will cause the implantable device(s) to be dispensed into the void or IM canal of the patient as the guide tube is retracted.

Alternatively, the devices may simply be digitally inserted into the void or IM canal of the patient by the surgeon.

The longitudinal channels of adjacent implantable devices do not need to be aligned with each other in order to provide a continuous pathway for the displacement and exit of the contents of the void or IM canal. This is due to the convex, domed or semispherical shaped ends of the implantable device which allows for the continuous flow of the contents of the void or IM canal to the adjacent implantable device.

Thus described is a device for implantation into a bone void (IM canal) or bone defect of a patient. The implantable device typically has a capsule shape; cylindrical with convex, domed or semispherical shaped ends, and a longitudinal channel or channels running end-to-end within the implantable device. The particular geometric features ensure a continuous exit path from the distal end of the first implantable device to the proximal end of the last implantable device. Thus, when serially inserted into a void or IM canal, it allows for the displacement of the void or IM canal contents. The contents of the void or IM canal can be blood, marrow, fat, air or any other fluid which may be present and occupy the void prior to insertion of the implantable device. The implantable device(s) are axially orientated for insertion into a void or IM canal where the presence of a continuous exit path is independent of the circumferential orientation of adjacent implantable devices. The implantable device may be made from bone substitute material and may include a medicament contained therein to provide a therapeutic function.

A range of bone substitute materials may be used in the present invention including but not limited to calcium-based bone substitute materials which may be used as bone void fillers and carriers for delivery of therapeutic agents to a bone void or defect. The bone substitute material, such as calcium sulfate, is typically supplied in the form of a powder which when mixed with a liquid component forms a hard-enable cohesive mass that can be moulded into shapes then allowed to cure undisturbed and finally set to form an implantable device.

Also provided in accordance with the present invention is an arrangement of the implantable devices described herein, the arrangement comprising a plurality of the devices lined up end to end. As desired, the longitudinal channels may or may not be axially aligned with each other.

This arrangement of the devices of the present invention is to be inserted and used in the bone void e.g. IM canal of a patient.

According to a further embodiment of the invention, there is provided a method of making an implantable device as defined hereinabove, wherein the implantable device is made by either casting the implantable device in a mould, or by 3D printing.

According to a further embodiment of the invention, there is provided a kit of parts for the production and delivery of implantable devices to an intramedullary canal of a patient; the kit of parts including a multi-cavity flexible mould mat, a guide tube, a pusher that facilitates the implantable devices being freely inserted into the intramedullary canal, a bone substitute powder component and liquid component, together with apparatus to enable mixing of the components and dispensation of the mixed components to cavities in the mould mat, where it is allowed to cure or set. The guide tube may be filled with one or more implantable devices.

The guide tube and pusher may each independently be non-rigid, i.e. they may be made of a material that allows it to bend or flex without fracture when a bending force is applied.

The IM Canal may be reamed in order to accommodate the placement of the implantable device(s) herein described Definitions In this specification, the following words and expressions, if and when used, have the meanings ascribed below:

"Axial centreline" means an imaginary line through the centre of the device, extending along the length thereof and following an axis of symmetry.

"Bioresorbable" refers to a material which resorbs in the body.

"Bone cement" or "cement" means a non-resorbable material including but not limited to PMMA for the treatment of bone disorders and filling of bone voids, defects or IM canal of the skeletal system.

"Bone void filler" or "bone substitute material" or "bone substitute" means a bioresorbable material, including but not limited to calcium sulfate or calcium phosphate, which is used for the treatment of bone disorders and filling bony voids or defects of the skeletal system to permit regeneration of natural bone growth in the skeletal system.

"Bone void" or "void" are interchangeable and mean any defect, cavity or gap of the skeletal system caused by trauma, disease or surgery.

"Capsule" defines a geometric shape comprising a cylindrical body with convex ends, sometimes described as a spherocylinder.

"Capsule or Spherocylindrical" means a three dimensional shape where one or more surfaces are semispherical and another surface is cylindrical.

"Cavity" or "device cavity" means a cavity within a mould for producing a bone substitute material device.

"Channel" describes a gap in an object which generally extends the full length or width of the object and allows for the passage of fluid.

"Comprising" or any cognate word specifies the presence of stated features, steps, or integers or components, but does not preclude the presence or addition of one or more other features, steps, integers, components or groups thereof. The expressions; "consists of" or "consists essentially of" or cognates may be embraced within "comprises" or cognates, wherein "consists essentially of" permits inclusion of substances not materially affecting the characteristics of the composition to which it applies.

"Digitally" means the placement of implantable devices into a void or IM canal by hand.

"Embolism" or "embolization" means to block or occlude blood vessels.

"Device" or "implantable device" describes a component for implantation into a void or IM canal.

"Device mould" describes a mould for the production of bone substitute material devices. It may contain one or, more preferably, a plurality of cavities.

"Fat embolism" is a medical condition where a fat particle or droplet passes into a patient's bloodstream and subsequently lodges within a blood vessel and blocks the blood vessel.

"Flexible" means where something is capable of bending easily without breaking.

"Hardenable bone substitute material" means a composition comprising a bone substitute material as defined herein and a hardening agent, e.g. an aqueous solution, which upon hardening (i.e. fully setting) forms bone void filler as defined herein. Typically, the hardenable bone substitute material is in the form of a workable paste.

"Intramedullary canal" or "IM canal" are interchangeable and mean the inside of a bone, typically the marrow cavity of a long bone.

"Long bone" means bones of a patient that provide strength, structure and mobility. Long bones are normally hard and dense and include but are not limited to the tibia, femur and humerus.

"Longitudinal" refers to a direction parallel to the long/cylindrical axis of the device.

"Longitudinal channel" describes an aligned channel or a plurality of channels that extends continuously the full length of the implantable device.

"Mould"—(noun) describes a tool with a hollow space or cavity which is used to impart the desired form to the product being moulded. The cavity or cavities are filled with a flowable material which subsequently hardens to produce solid components having a shape defined by the shape of the mould cavity.

"Mould mat" means a generally flat and flexible mould having a plurality of cavities to accept bone substitute material in a mouldable paste condition and contain the bone substitute material or cement therein for a time sufficient to allow hardening of the cement to give set capsule shaped devices prior to their extraction.

"Non-rigid" describes the mechanical property of a material that allows it to bend or flex without fracture when a bending force is applied.

"Patient" means a human or animal subject that is receiving or is to receive medical treatment.

"Petechial rash" means round spots or pinpoints that appear on the skin of a human or animal subject as a result of bleeding occurring under the subject's skin.

"PMMA" means poly (methyl methacrylate).

"Semispherical" means 'not completely spherical' and describes a geometric shape which is formed when a sphere is intersected by a plane.

"Surgeon" means a medical practitioner qualified to practise surgery on a human or animal subject.

BRIEF DESCRIPTION OF THE DRAWINGS

The various features of the invention, which are applicable as appropriate to all aspects, will now be described in more detail with reference to the following drawings, where.

DETAILED DESCRIPTION OF DRAWINGS

Figure 1:
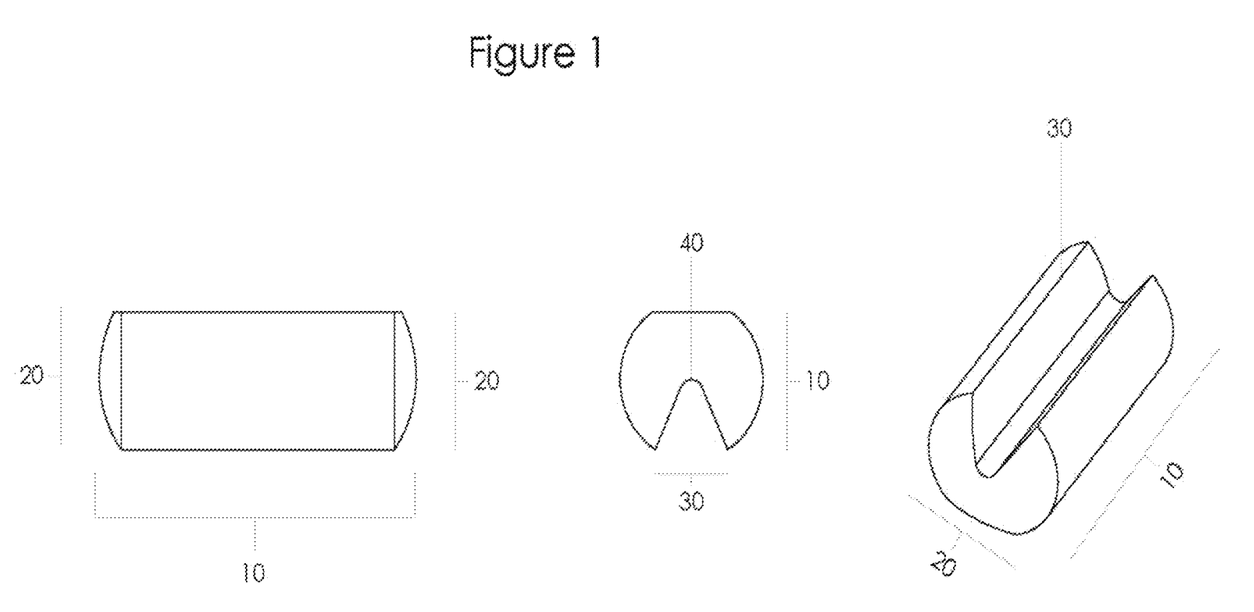
FIG. 1 shows plan, end and isometric views of the implantable device of the invention with a spherocylindrical or capsule shape and a longitudinal channel.

FIG. 1 shows an implantable device 10 of the present invention, which is capsule shaped, having domed, convex or semispherical shaped ends 20. A longitudinally aligned channel 30 intersects the surface of the implantable device and extends towards the cylindrical axis 40 of the implantable device.

Figure 2A:
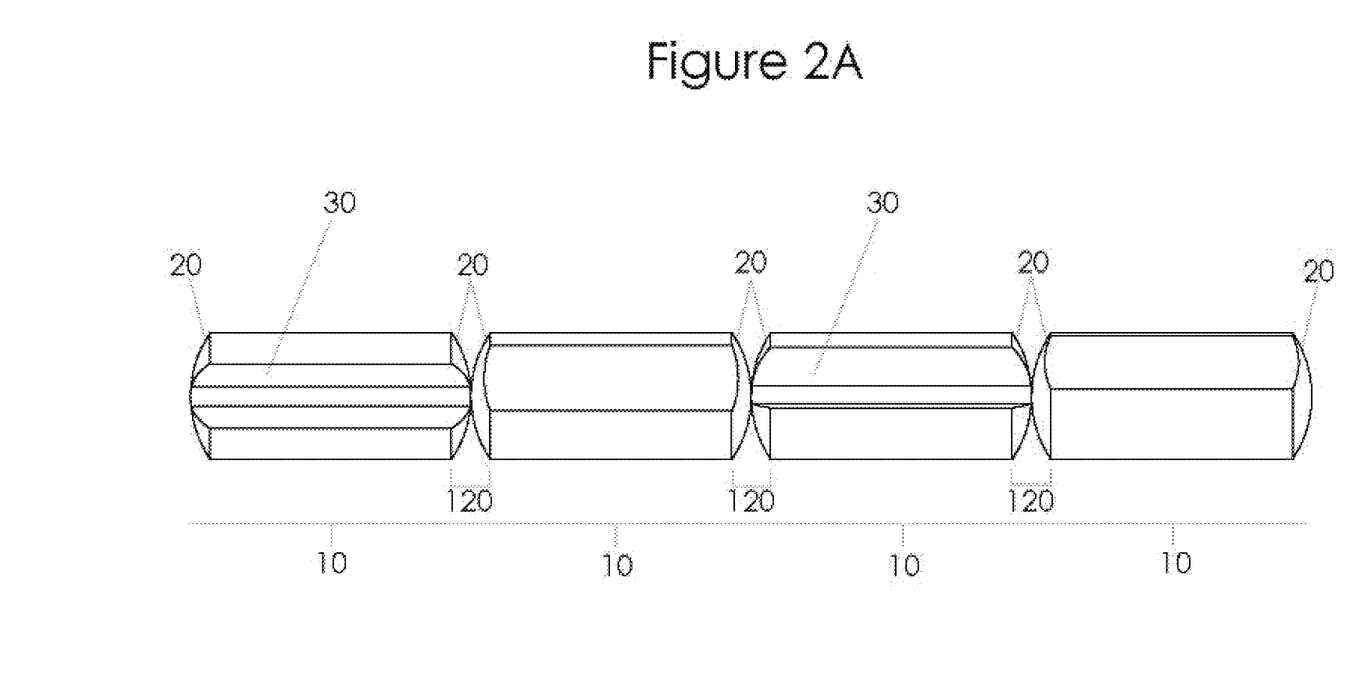
FIG. 2A shows multiple implantable device(s) of the present invention together in series.

FIG. 2A shows multiple implantable devices 10 of the present invention together in series, which are generally capsule shaped, having domed, convex or semispherical shaped ends 20, where the ends 20 create a gap at the exterior 120 of the ends 20 of the implantable device 10. There is no need to have the longitudinal channel 30 of any particular implantable device 10 aligned with the longitudinal channel 30 of an adjacent implantable device 10.

Figure 2B:
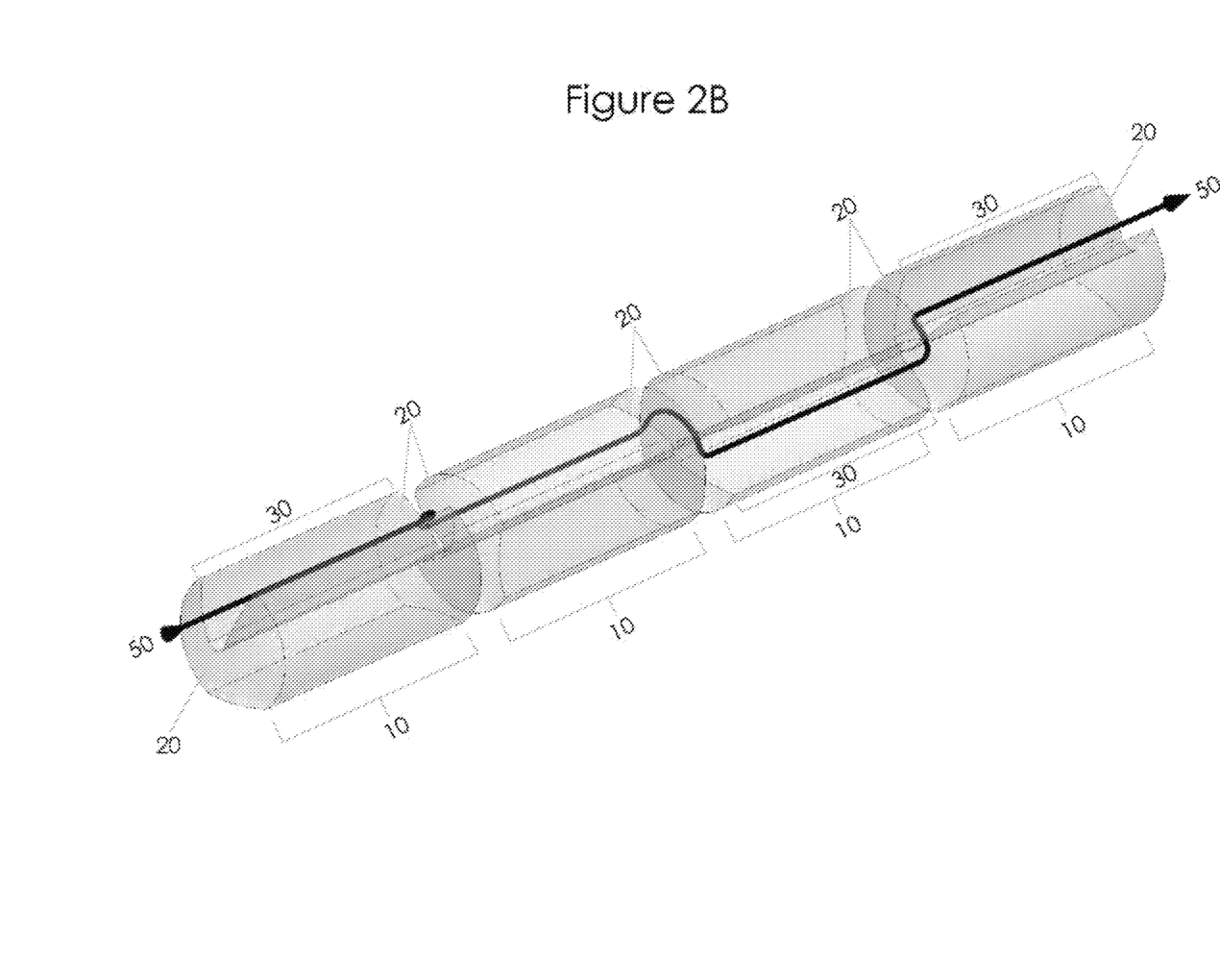
FIG. 2B shows multiple implantable device(s) of the present invention together in series, and how the contents of the bone void or IM canal can be displaced and move through the channel.

FIG. 2B shows multiple implantable devices 10 of the present invention together in series, showing the venting channel 30 for the contents of the bone void or IM canal 50 through the longitudinal channel 30 and domed, convex or semispherical shaped ends 20.

FIG. 3A shows a multi-cavity flexible mould mat 60 which has cavities 70 in rows 80. Each cavity has a shape that corresponds to the shape of the implantable device 10.

FIG. 3B shows a cross-sectional view of the multi-cavity flexible mould mat 60, of a row of cavities 80. The shape of the cavities 80 corresponds to that of the implantable devices 10, with the longitudinal channels 30 visible.

However, while the multi-cavity flexible mould mat 60 constitutes a typical method of manufacturing the implantable devices 10, the implantable devices 10 may be alternatively produced by a method not described herein, by methods which will be readily apparent to the person skilled in the art.

Figure 4:
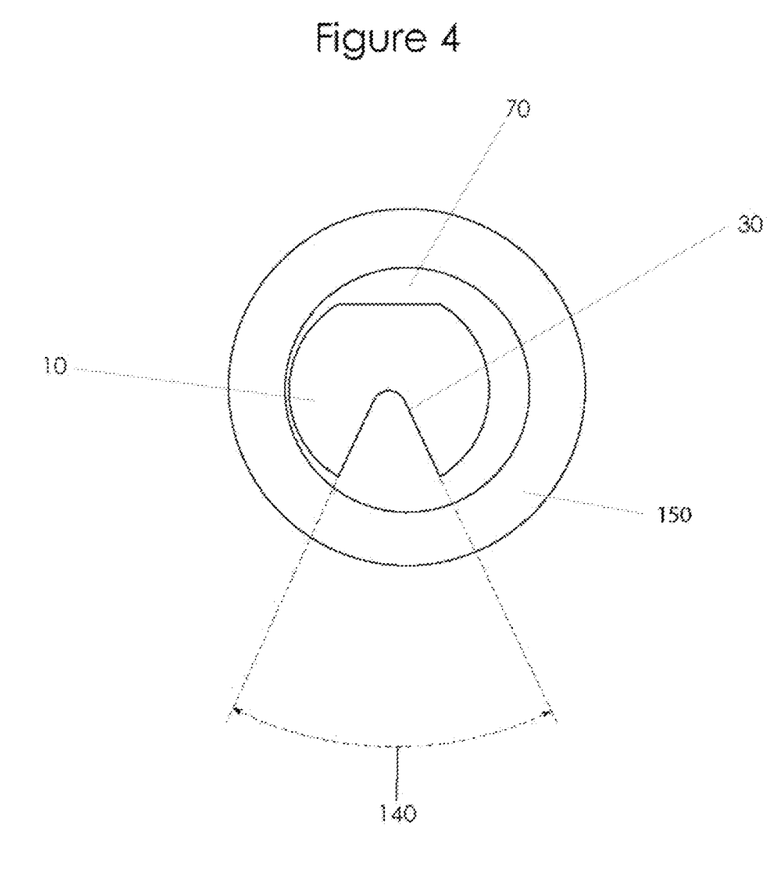
FIG. 4 shows a sectional view of the implantable devices as it may appear in a bone void or IM canal.

FIG. 4 shows a sectional; representation of an IM canal 70 and cortex 150, containing an implantable device 10 that has been inserted therein. The longitudinal channel 30 has a taper angle 140.

Figure 5:
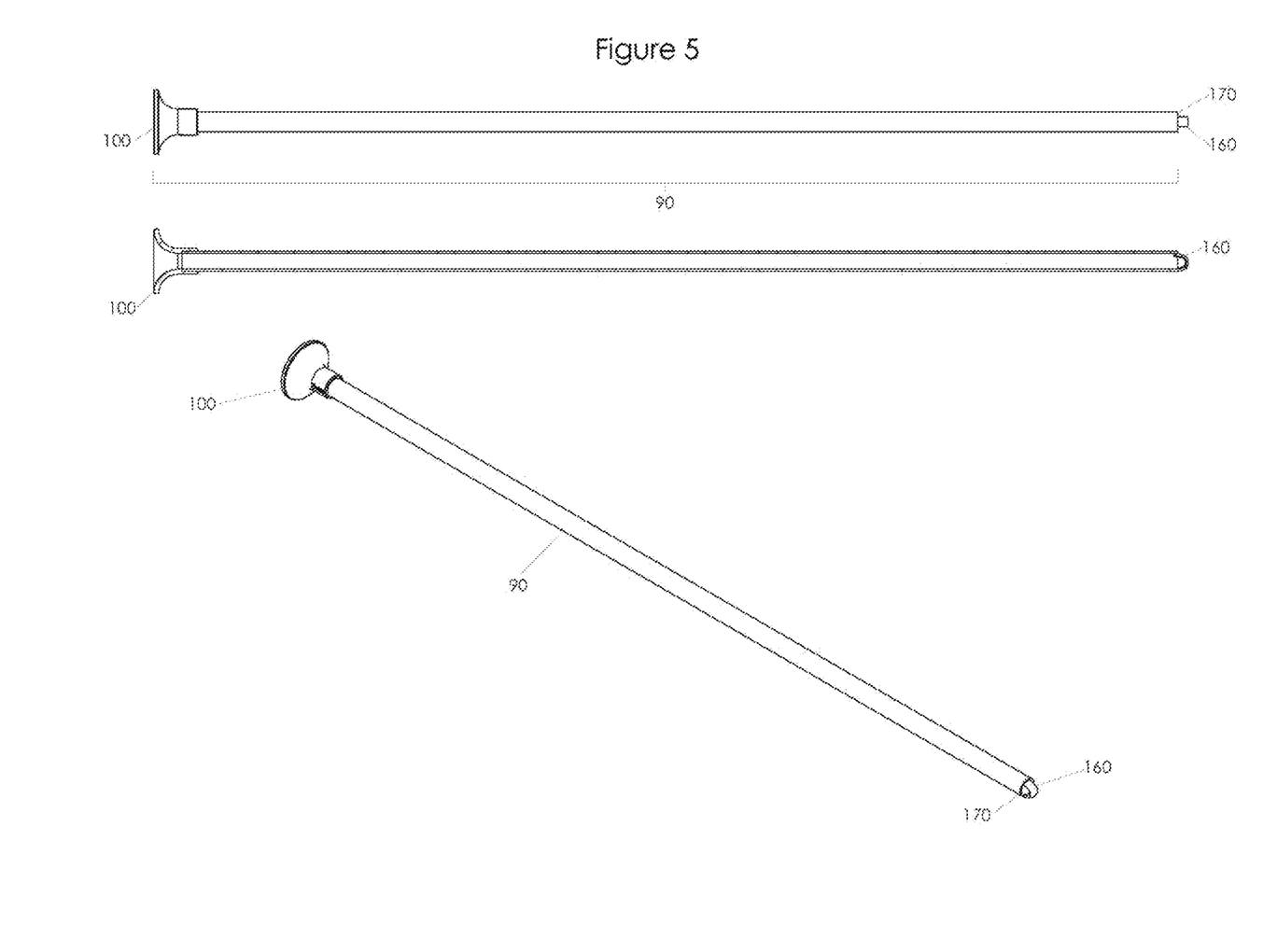
FIG. 5 shows an example of a guide tube.

FIG. 5 shows a guide tube 170 for the insertion of the implantable devices in the bone void or IM canal with a funnel at one end 100. The outside diameter of the guide tube 170 is less than the inside diameter of the medullary canal to be treated. The distal end of the guide tube 170 has a flexible retainer 160 which retains the implantable devices 10 within the guide tube 170 until pressure is applied by the pusher 110 to the implantable devices 10 which will cause the retainer to flex allowing the implantable devices 10 to exist the guide tube 170.

Figure 6:
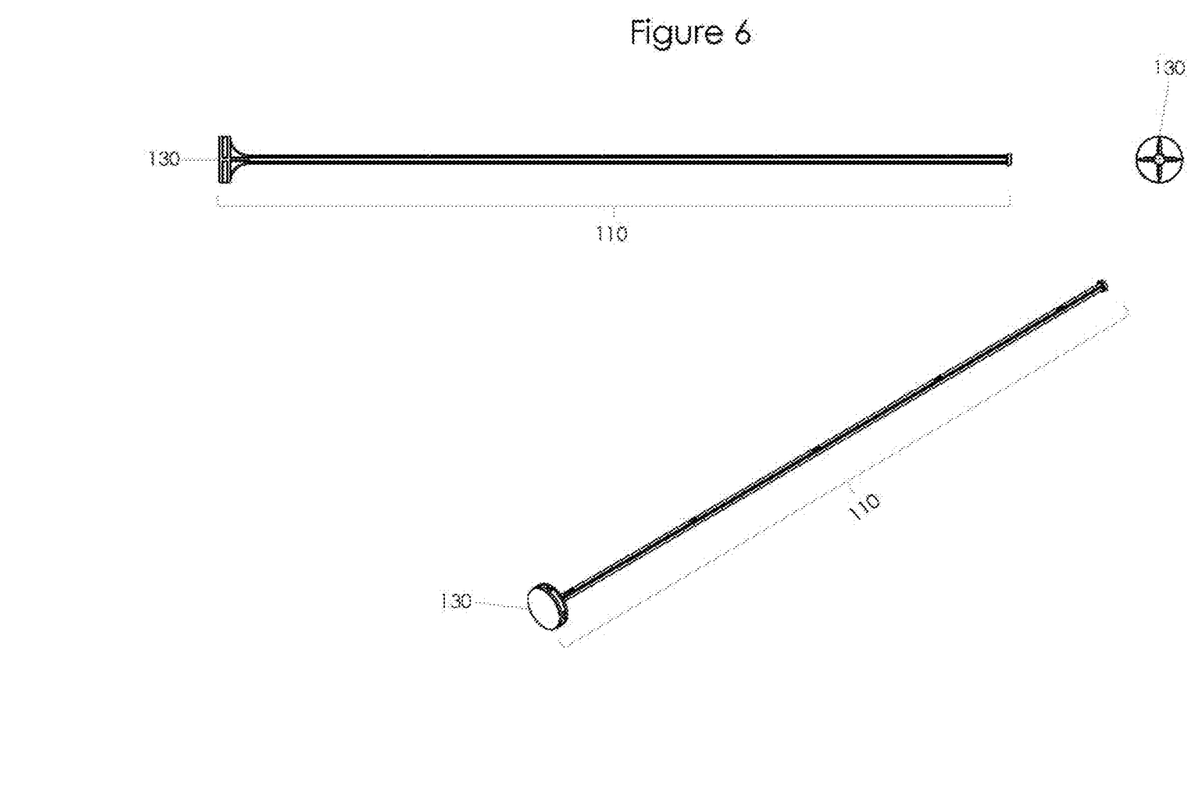
FIG. 6 shows an example of a pusher that may be used with the guide tube.

FIG. 6 shows a pusher 110, where the diameter of the pusher 110 is less than the internal diameter of the guide tube 170. The pusher 110 has a circular handle 130, to allow the Surgeon to maintain pressure on the implantable devices 10 whilst retracting the guide tube 170. It is to be understood that various modifications may be made to the device disclosed herein without departing from the scope of the invention.

The longitudinal channel cross section may be semicircular.

The longitudinal channel cross section may be a straight line.

The longitudinal channel may have some other shape.

Bone cement may be used to form the implantable devices.

It is of course to be understood that the present invention is not intended to be restricted to the foregoing examples which are described by way of example only.

REFERENCES

1. Shamsuddin, Akhtar, MD (2009) Fat Embolism
2. Issack, Paul S. MD, PHD et al., Fat Embolism and Respiratory Distress Associated with Cemented Femoral Arthroplasty, The American Journal of Orthopedics.
3. Shaikh N; Emergency management of fat embolism syndrome. J Emerg Trauma Shock. 209 January; 2(1):29-33.
4. http://jcp.bmj.com/content/s3-4/1/121.full.pdf+html
5. Rebellow M M et al, Venting Alone is Insufficient in Preventing Complications in the Prophylactic Nailing of Femoral Metastases; Orthopaedic Biomechanics Laboratory, Sunnybrook & Women's College Health Sciences Centre, Toronto, Ontario, Canada; 49th Annual Meeting of Orthopaedic Research Society; Poster #0997.
6. http://www.patient.co.uk/doctor/fat-embolism-syndrome

The invention claimed is:

1. An implantable device for insertion into a bone void, the implantable device comprising a bone substitute material and having a cylindrical body and one or more longitudinal channels extending the entire length of the device, where said one or more longitudinal channels allows for depressurisation of the bone void during implantation of the device; the one or more longitudinal channels each intersecting a surface of the device and extending to an axial centerline thereof, and being tapered such that the width of the one or more longitudinal channels opening on an outer, circumferential edge of the implantable device is greater than its width at a base thereof; and wherein the devices have a flat surface on an opposing longitudinal side to the one or more longitudinal channels; and wherein the device has convex, domed or semispherical shaped ends.

2. An implantable device according to claim 1, wherein the one or more longitudinal channels allows for the displacement and/or exit of the void contents.

3. An implantable device according to claim 1, wherein the one or more longitudinal channels tapers in width from the exterior circumference towards its central axis.

4. An implantable device according to claim 3, wherein the one or more longitudinal channels has a taper angle of 10 degrees to 145 degrees.

5. An implantable device according to claim 4, wherein the taper angle of one or more longitudinal channels is from 20 degrees to 50 degrees.

6. An implantable device according to claim 1, wherein an opposing surface to one or more longitudinal channels has a flat surface.

7. An implantable device according to claim 1, wherein the device has a capsule shape, having one or more longitudinal channel intersecting the surface of the device and extending the full length of the device and also extending towards the device centreline.

8. An implantable device according to claim 1, wherein the displacement of the void contents minimises an increase in pressure within the void.

9. An implantable device according to claim 1, wherein the bone substitute material comprises a calcium-based bone substitute material.

10. An implantable device according to claim 1, wherein the implantable device is adapted for insertion into a void that is within an intramedullary canal of a patient.

11. An implantable device according to claim 10, wherein the implantable device is adapted for insertion into a void comprising a defect in bone.

12. An arrangement of two or more implantable devices comprising a plurality of the devices lined up end to end, wherein each of the implantable devices comprises a bone substitute material and has a cylindrical body and one or more longitudinal channels extending the entire length of the device, where said one or more longitudinal channels allows for depressurisation of the bone void during implantation of each device; the one or more longitudinal channels each intersecting a surface of each device and extending to an axial centerline thereof, and being tapered such that the width of the one or more longitudinal channels opening on an outer, circumferential edge of each implantable device is greater than its width at a base thereof; and wherein the devices have a flat surface on an opposing longitudinal side to the one or more longitudinal channels; and wherein each device has convex, domed or semispherical shaped ends.

13. An arrangement according to claim 12, wherein the longitudinal channels are axially aligned with each other.

14. An arrangement according to claim 12, wherein the longitudinal channels are not axially aligned with each other.

15. An arrangement according to claim 12, wherein the arrangement is adapted for insertion into an intramedullary canal of a patient.

16. An implantable device according to claim 1, wherein the one or more longitudinal channels extend the full length of the device.

* * * * *